US006994798B2

(12) United States Patent
Buri et al.

(10) Patent No.: US 6,994,798 B2
(45) Date of Patent: Feb. 7, 2006

(54) PHENOLATE-CONTAINING FORMULATION WITH LOW FREEZING POINT

(75) Inventors: Matthias Buri, Rothrist (CH); Patrick Schwarzentruber, Starrkirch-Wil (CH)

(73) Assignee: Omya AG, Oftringen (CH)

( * ) Notice: Subject to any disclaimer, the term of this patent is extended or adjusted under 35 U.S.C. 154(b) by 0 days.

(21) Appl. No.: 10/275,861

(22) PCT Filed: Apr. 26, 2001

(86) PCT No.: PCT/EP01/04729

§ 371 (c)(1),
(2), (4) Date: Jun. 9, 2003

(87) PCT Pub. No.: WO01/85659

PCT Pub. Date: Nov. 15, 2001

(65) Prior Publication Data

US 2004/0023939 A1     Feb. 5, 2004

(30) Foreign Application Priority Data

May 12, 2000 (DE) ............... 100 23 458
Jun. 2, 2000 (DE) ............... 100 27 588

(51) Int. Cl.
C07C 39/235 (2006.01)
C07C 39/44 (2006.01)
C07C 37/88 (2006.01)
A01N 31/08 (2006.01)
C09K 15/08 (2006.01)

(52) U.S. Cl. ............ 252/70; 106/15.05; 106/16; 106/18.35; 106/499; 106/500; 162/161; 252/73; 252/74; 252/75

(58) Field of Classification Search .......... 106/15.05, 106/16, 18.35, 499, 500; 162/161; 252/70, 252/73, 74, 75

See application file for complete search history.

(56) References Cited

U.S. PATENT DOCUMENTS 3,824,190 A * 7/1974 Winicov et al. ........... 514/736
5,837,274 A * 11/1998 Shick et al. ............... 424/406
6,019,941 A * 2/2000 Porcello .................... 422/4
6,362,152 B1 * 3/2002 Young et al. .............. 510/386
6,569,229 B1 * 5/2003 Buri et al. ................. 106/15.05

FOREIGN PATENT DOCUMENTS

| DE | 2063631 A1 | * | 7/1971 |
| DE | 2732441 A1 | * | 2/1979 |
| DE | 42 02 051 | | 7/1993 |
| WO | WO98/17773 A1 | * | 4/1998 |

OTHER PUBLICATIONS

Derwent Abstract No. 1975-42201W, abstract of Soviet Union Patent Specification No. 436812A (Jan. 1975).*
Derwent Abstract No. 1989-318135, abstract of Spanish Patent Specification No. 2006998A (May 1989).*

* cited by examiner

Primary Examiner—Anthony J. Green
(74) Attorney, Agent, or Firm—Oblon, Spivak, McClelland, Maier & Neustadt, P.C.

(57) ABSTRACT

The present invention discloses an aqueous phenolates-containing liquid formulation having a solidification point of less than or equal to −10° C. which is characterized by comprising the following components:

a) 50–80% by wt. of one or more phenolates;
b) 0.1–10% by wt. of at least one crystallization inhibitor; and water and optionally other components forming the balance.

29 Claims, No Drawings

PHENOLATE-CONTAINING FORMULATION WITH LOW FREEZING POINT

The present invention relates to an aqueous liquid phenolates-containing formulation having a solidification point which is less than or equal to minus 10° C., a method for the preparation thereof, an aqueous suspension or dispersion containing said formulation as well as different industrial applications of said formulation.

Formulations of phenolate derivatives have deficiencies, in particular with respect to their use as preservatives in the technical field, such as in highly concentrated pigment slurries. Salts of phenol, of alkyl and aryl substituted phenols, of halogenated phenols as well as of cresols and halogenated cresols are known as fungicidal and bactericidal agents in the protective and curative fields. The majority of formulations of said phenolates are water-soluble alkali salt formulations which are too alkaline for the later intended use, and therefore have a negative effect on the product to be protected; or have a freezing point of 0° C. or only just below 0° C.; or tend to crystallize at low temperatures and in high concentrations especially upon seeding with seed crystals; or contain high amounts of organic solvents or high amounts of excess alkali.

In particular, sodium o-phenylphenolate and potassium o-phenylphenolate are known as fungicidal agents for wood and also as preservatives for pigment slurries. Sodium o-phenylphenolate and potassium o-phenylphenolate may be obtained in the form of powders. Furthermore, sodium o-phenylphenolate is commercially available in the form of a 25% by wt. caustic soda solution and in the form of a 35–38% by wt. emulsion wherein high amounts of emulsifying agents are used for the stabilization thereof. Potassium o-phenylphenolate is commercially available in the form of a 35–39% by wt. caustic potash solution containing 38% by wt. of potassium o-phenylphenolate and 6–10% by wt. caustic potash in water.

Recently, DE 198 59 136.5 has described partially neutralized forms of o-phenylphenol/alkali o-phenylphenolate in water and high amounts of organic solvents such as glycols and aromatic alcohols. DE 42 02 051 A1 also describes highly concentrated liquid forms of the phenol derivative series. However, these are not present in the neutralized form, have melting points of more than +15° C. and are water insoluble.

It is difficult to handle sodium o-phenylphenolate in powder form in higher amounts. Liquid formulations are clearly preferred.

The transport and storage costs of 25% by wt. aqueous sodium o-phenylphenolate are high. It is impossible to achieve higher concentrations since its solubility is too low. Also in concentrations of only 25% the product tends to crystallize at room temperature. Spontaneous crystallization occurs at temperatures below 0° C. Potassium o-phenylphenolate in concentrations of 35–39% by wt. which contains a high excess of caustic potash is extremely caustic and has a pH of much more than 12. To prevent crystallization at minus 10° C., caustic potash must be present in a one to 30% excess. Upon addition to an aqueous pigment slurry having a high solids content, particularly at solids concentrations of >50 vol. %, this high pH as well as the high ion concentration result in the formation of agglomerates in the pigment slurry as well as in an altered pH of the final product.

If insufficiently sheared during admixing, the partially neutralized phenolates described in DE 198 59 136.5 dissolved in water and glycols tend to form agglomerates, show separation of the aqueous pigment slurry and the partially neutralized phenolate solution and flotation thereof on the surface of the slurry. Therefore, no optimal preservation is obtained in this case and the result may be deposits of phenolates in the ducts. In addition, the high proportion of organic solvents in the range of 20–90% by wt. is not desirable for some applications.

The use of emulsified sodium o-phenylphenolate in pigment slurries having a high solids content bears a risk because the emulsifying agent destabilizes the pigment dispersion and tends to form foams. Furthermore, most of the aqueous salt solutions and aqueous emulsions of o-phenylphenol have freezing points at or just below 0° C. Only potassium o-phenylphenolate containing KOH in a high excess has a freezing point of minus 15° C. However, this compound bears the risk of altering the pigment slurry—properties such as formation of agglomerates and raising of the pH. During the winter in Northern Europe, e.g. in Norway, and in North America and Canada, it is impossible to transport aqueous liquids having solidification points around the freezing point without risking the freezing thereof if no heating is installed in the transport container. The same problem applies to storage. Moreover, it is economically as well as ecologically unreasonable and not accepted by the industry to transport solutions in such low concentrations over long distances.

It is an object of the present invention to provide a liquid formulation of phenolates having a freezing point or solidification point, respectively, of less than or equal to −10° C. wherein the solvent system thereof contains a major proportion of water.

According to the present invention, this object has been solved by the liquid aqueous phenolates-containing formulation characterized in more detail in claim 1 which has a solidification point of less than or equal to −10° C. The formulation described herein comprises the following components:

a) 50–80% by wt. of one or more phenolates;
b) 0.1–10% by wt. of at least one crystallization inhibitor; and water and optionally other components forming the balance.

Preferred embodiments of the present invention are obvious from the dependent claims and the alternative independent claims as well as from the following specification.

The formulation according to the present invention is characterized by containing phenolates in a concentrated form of 50–80% by wt. based on the total formulation. Phenolates means salts of phenols which dissolve in water accompanied by an alkaline reaction. Phenols is the generic term for aromatic hydroxy compounds wherein the hydroxy groups are directly bound to the benzol nucleus. Examples of phenols are phenol itself and phenols containing one or more aliphatic and/or aromatic substituents. Examples for these are o-phenylphenol, cresols and resorcinols. In the present formulation, the phenols and their derivatives are present in their completely neutralized form as salts, i.e. in the form of phenolates.

Furthermore, the formulation according to the present invention preferably has a phenolate content, calculated as the corresponding phenol or phenol derivative, respectively, of more than 40% by wt. The phenolate solution, preferably o-phenylphenolate, is neutralized to 103–115 mol %, based on the phenolate, preferably by means of alkali hydroxides. This means that 1.03–1.15 mols of alkaline substance, preferably alkali hydroxide, per mol of phenolate are added to the phenolate solution. It is particularly preferred to use 105 mol % of KOH, based on the phenolate content, for neutralization.

The phenolates employed according to the present invention exhibit an antimicrobial effect and therefore act as preservatives. Due to these properties, the formulations according to the present invention may be employed both for protective and for curative uses.

Preferred phenolates are phenolates having one ore more aliphatic and/or aromatic substituents. Examples of such derivatives which may be used according to the present invention are o-phenylphenolate, halogenated phenolates, cresol salts, salts of halogenated cresols and salts of resorcinols or the mixtures thereof. Examples of cresol salts are salts of halogenated cresols, in particular salts of chlorinated cresols, salts of o-, m-, and p-cresol, salts of isopropyl o-cresol, salts of 4-isopropyl m-cresol. An example of a useful resorcinol salt is a salt of 4-n-hexyl resorcinol.

The phenolates are present in amounts of 50–80% by wt. wherein it should be understood that all ranges between 50 and 80% by wt. are also comprised by the present invention. Preferred ranges are 55–75% by wt., 55–70% by wt., 60–70% by wt., 60–65% by wt. and particularly preferred 65% by wt., each based on the total formulation.

In a preferred embodiment of the present invention, the phenolate solution has been neutralized by alkali hydroxides so that the phenolates are preferably present as the potassium salt, potassium and sodium salt and/or potassium and lithium salt. Particular preferred, the phenolates are present as the potassium salt.

The solvent system for the phenolates preferably contains an excess of 0.03–0.15 mols of alkali hydroxides. Preferably, 1.03–1.15, further preferred 1.05–1.10 mols of alkali hydroxides per mol of phenolate are used for neutralization. The degree of neutralization with alkali hydroxide, preferably potassium hydroxide, is 102–115 mol %, preferably 103–107 mol % and particularly preferred 105 mol %, based on the phenolate.

Important for the success of the present invention has been the surprising and unforeseeable effect of low amounts of alcohols which unexpectedly act as crystallization inhibitors.

As the crystallization inhibitors there are used organic water-soluble substances, preferably alcohols, in amounts of 0.1–10% or mixtures thereof, e.g. in amounts of 1 to 5% by wt.

As the crystallization inhibitors there are preferably used one or more aliphatic glycol compound(s) such as ethylene glycol, monopropylene glycol and/or diethylene glycol, and/or one or more aliphatic alcohol(s) such as methanol, ethanol, n-, iso-propanol, isomers of butanol, such as 1-butanol, and/or of pentanol, and/or one or more aromatic alcohol(s) such as benzyl alcohol, 2-phenylethane-1-ol, 3-phenylpropane-1-ol and/or 1-phenylpropane-2-ol.

The crystallization inhibitors are present in an amount of 0.1–10% by wt, based on the total formulation. Preferred amounts are 0.5–5.0% by wt, further preferred 1–3% by wt., based on the total formulation, wherein it should be understood that all ranges between 1 and 10% by weight may also be used.

Examples of aromatic alcohols which may be preferably used are:
benzyl alcohol and/or 2-phenylethane-1-ol and/or 3-phenylpropane-1-ol and/or 1-phenylpropane.

Examples of monovalent aliphatic alcohols which may be preferably used are:
methanol, ethanol, propanols, butanols, pentanols.

Examples of aliphatic glycols which may be preferably used are:
ethylene glycol, propylene glycol, butanediols, pentanediols.

The phenolate content of the formulation according to the present invention preferably is more than 40% by wt., calculated as the corresponding phenol or phenol derivative, respectively. The phenolate solutions wherein o-phenylphenolate is especially preferred, are neutralized to 103–115 mol %, based on the phenolate, preferably with alkali hydroxides, in particular with KOH. In a preferred embodiment, 105 mol % of KOH, based on the phenolate content, are employed for neutralization.

Besides phenolates and crystallization inhibitors which comprise a proportion of 50.1–90% by wt., the formulation according to the present invention also contains 10–49.9% by wt. of water as well as optionally other constituents such as other agents having an microbicidal effect (antimicrobial) or substances promoting agents which have an microbicidal effect.

The formulation according to the present invention is an aqueous formulation wherein the solvent system comprising a proportion of 20–50% by wt. of the formulation contains 90–99% by wt. of water. The crystallization inhibitors are components of the solvent system and are present in an amount of 0.1–10% by wt., based on the solvent system. However, within these limits it is also possible to replace a proportion of the water or the crystallization inhibitor, respectively, by other components, for example by other microbicidal (antimicrobial) agents and substances promoting microbicidal (antimicrobial) agents. Particularly preferred as the agents having an antimicrobial effect are: amines, primary and/or secondary and/or tertiary and/or quatemary amines and/or diamines, preferably primary and/or secondary and/or tertiary and/or quatemary fatty amines and/or diamines, wherein one or more substituents on the nitrogen have a chain length of 10 to 20 carbons, preferably 10 to 18 carbons. Examples are dodecylamine, didocecylamine, didodecylmethylamine, didodecylbenzylmethylammonium chloride, or the substances dicocomethylbenzylammonium chloride, N-tallow-1,3-diaminopropane. The primary and/or secondary and/or tertiary fatty amines and/or the amines may also be present in the form of salts. As neutralization agents for the primary and/or secondary and/or tertiary amines and/or the diamines there may be used mineral acids and/or organic acids wherein formic acid and/or acetic acid are preferably employed. Another example of an antimicrobial agent is tributyl tin benzoate. Examples of substances promoting antimicrobial agents such as chelating agents, preferably nitrolortiacetic acid, ethylenediaminetetraacetic acid, DTPA, and the alkali salts thereof and optionally one or more oxidation stabilizers such as 2-phosphono-1,2,4-butanetricarboxylic acid, preferably in amounts of 0.05–1.0% by wt.

In a formulation containing phenolate in an amount of 60–70% by wt. the crystallization inhibitors are preferably present in an amount of 1–3% by wt., based on the total formulation.

In another embodiment of the present invention the phenolates are present in the formulation in an amount of 50–80% by wt., preferably 55–70% by wt., and one or more aliphatic glycol compounds and/or glycerol and/or one or more aliphatic and/or aromatic alcohols in an amount of 0.1–10% by wt., preferably 1–5% by wt. are present as the crystallization inhibitors wherein the total amount of crystallization inhibitors is at maximum 10% by wt., and the balance with respect to 100% by wt. is formed by 0.03–0.15 mols/mol of excess alkali and water.

The phenolates contained in the formulation have an antimicrobial effect and therefore act as preservatives. Due to these properties they may be used both for protective and for curative applications. The formulation has the advantage that the phenolates show no spontaneous or gradual crystallization or that the crystallization thereof is at least so slow that it does not have an adverse effect.

The formulations according to the present invention have crystallization points or freezing points, respectively, of at least −10° C. even upon addition of seed crystals. Preferred embodiments of the formulations have crystallization points or freezing points, respectively, or −15° C. or even −20° C.

Thus the formulation is also characterized by containing:
a) 50–80% by wt. of at least one phenolate; and
b) 20–50% by wt. of a solvent system comprising 90–99.9% by wt. water and 0.1–10.0% by wt. of at least one crystallization inhibitor; wherein a proportion of 1.0–4.9% by wt. of said formulation may be replaced by other antimicrobial agents and/or other components.

Thus, important for the success of the present invention has been the surprising and unforeseeable effect of low amounts of alcohols which are employed in an amount of 0.1–10% by wt., based on the total formulation, and which unexpectedly act as crystallization inhibitors in said formulation.

In another embodiment of the present invention, the formulation contains other substances having an antimicrobial effect, for example compounds having a bactericidal and/or fungicidal effect.

Preferably, the formulation according to the present invention contains no emulsifiers, anion active, non-ionic surfactants or wetting agents, such as lauryl sulfate, nonyl phenols, ethoxylates, fatty amines, since these components may destabilize the suspensions or dispersions of minerals, fillers, pigments and natural or synthetic organic binders and the mixtures thereof, promote foaming and/or lead to depositions.

The formulations according to the present invention contain as organic solvent components besides the phenolate preferably at most 1–10% by wt., further preferred 1–5% by wt., also preferred 1–3% by wt. of organic solvent components. Organic solvent components relates here to the crystallization inhibitor including the further optionally contained components, such as microbicidal agents and/or substances promoting the microbicidal agents.

The preparation of the formulation according to the present invention may be performed by those skilled in the art using their expertise without need of an inventive step. For example, for the preparation of the formulation according to the present invention, water, the neutralizing agent, and the crystallization inhibitor and optionally other substances are charged into a vessel and the phenol is dissolved by agitation and optionally by heating.

Principally, there are no special requirements with respect to the order of addition. However, a temporary incompatibility may occur leading to a temporary precipitation of substances. Therefore, water and the neutralizing agent are preferably added first, and the phenol compounds are dissolved therein, followed by addition of the crystallization inhibitor.

It has been found out surprisingly and unexpectedly that phenolate solutions which have been completely neutralized, preferably neutralized to 103–115 mol % with alkali hydroxide, and solutions of phenolates or of salts of phenol and the derivatives thereof, e.g. o-phenylphenolate, or salts of cresol to which 0.1–10% by wt. alcohols, based on the total formulation, have been added as crystallization inhibitor showed no crystallization even at a high solids content of more than 50% by wt. of phenolates and at very low temperatures of e.g. −20° C. also if seed crystals such as solid o-phenylphenol were added several times, the solutions were stable for months, and the brown discoloration which formed was slighter than for example that which is well-known from conventional aqueous solutions of alkali salts of o-phenylphenol, and the freezing point is optimal for the object to be solved. Surprisingly, the same formulations of phenolates at concentrations of phenolates of e.g. only 40% by wt. are not stable against crystallization at −20° C. and show spontaneous solidification.

It is also obvious from the accompanying Examples, that the formulation according to the present invention is preferably employed as a preservative, particularly preferred for the preservation of aqueous suspensions or dispersions of minerals, fillers, pigments, and natural or synthetic organic binders and the mixtures thereof. Using the formulation according to the present invention, suspensions or dispersions having a solids content of more than 40% by wt., preferably more than 60% by wt., and further preferred more than 70% by wt. may also be treated at temperatures of <−10° C. without crystallization of the phenolates. Furthermore, the formulation may be employed in the preservation of cooling lubricants, preferably in the metal industry. The aqueous suspensions or dispersions of minerals, fillers and/or pigments containing the formulation according to the present invention are preferably employed in the fields of papermaking, paper coating, as well as aqueous lacquers and paints. The formulation is suitable for protective as well as curative use.

Furthermore, the aqueous suspension or dispersion may further contain one or more synthetic and/or natural organic binders, preferably styrene butadiene latices and/or styrene acrylate latices, starch and/or carboxymethylcellulose which are protected from microbial attack and/or spoilage.

Preferably, as the minerals and/or fillers and/or pigments the aqueous suspension or dispersion contains compounds containing elements of the second and/or the third main group and/or the fourth main group and/or the fourth side group of the period system of elements, particularly calcium and/or silicon and/or aluminium and/or titanium and/or barium, and/or organic pigments.

Preferably, the aqueous suspension or dispersion contains minerals and/or fillers and/or pigments containing kaolin and/or aluminium hydroxide and/or titanium dioxide and/or barium sulfate and/or polystyrene hollow spheres and/or formaldehyde resins and/or calcium carbonate, particularly natural calcium carbonates and/or precipitated calcium carbonates and/or marble and/or lime and/or dolomite and/or dolomite-containing calcium carbonates.

Thus, the present invention also relates to aqueous suspensions or dispersions of minerals and/or fillers and/or pigments and/or natural or synthetic organic binders and/or cooling lubricants containing the formulation according to the present invention. The proportion of the formulation in the aqueous suspension or dispersion preferably is 100 g of the formulation/ton of good to be preserved to 2500 g of the formulation/ton of good to be preserved.

In the following, the invention will be explained in more detail with respect to the Examples and also in comparison to the prior art. However, the invention is not intended to be limited to these exemplary embodiments.

GENERAL REMARKS WITH RESPECT TO THE EXAMPLES

1.) Germ Counts

The germ count was determined according to the method "Bestimmung von aeroben mesophilen Keimen", Schweizerisches Lebensmittelbuch, chapter 56, section 7.01, edition of 1985, revised version of 1988. Mostly, the bacterial strains detected were from the family of pseudomonads (predominantly *Pesudomonas aeruginosa*), but also gram-positive germs as well as fungi were present.

2.) Measurement of the Viscosity of the Mineral and/or Filler and/or Pigment Suspension The measurement of the viscosity was performed on a Brookfield viscosimeter type PVF-100 at 100 rpm. The following spindles were used for the individual measurements:

| Spindle | | |
|---|---|---|
| | RV2 | 40–320 mPas |
| | RV3 | 320–800 mPas |
| | RV4 | 800–1600 mPas |
| | RV5 | 1600–3200 mPas |
| | RV6 | 3200–8000 mPas |

The measurement was carried out in a low 400 ml beaker.

The temperature during the measurement was 20° C. The measurement was performed after stirring for 1 min.

Prior to the actual measurements, all samples were stirred intensively for 2 min (5000 rpm, stirring disc diameter 50 mm).

This type of viscosity measurement was used in all of the following examples.

3.) Fineness of the Mineral and/or Filler and/or Pigment Suspension

The fineness characteristics of the suspensions prepared according to the present invention were determined by sedimentation analysis in a gravity field using a SEDIGRAPH 5100 device from Micromeritics company, U.S.A.

The measurement of the cation-stabilized suspensions was carried out in distilled water. Dispersion of the samples was performed by means of high-speed stirrer and sonication.

Measurements on the powders were performed in 0.1% solution of $Na_4P_2O_7$.

The particle distribution measured was depicted on a x-y recorder as the cumulative undersize frequency curve (see e.g. Belger, P., Schweizerische Vereinigung der Lack-und Farbenchemiker, XVII. FATIPEC-Kongress, Lugano, Sep. 23–28, 1984) the x-axis representing the particle diameter of a corresponding spherical cross section and the y-axis representing the amount of particles in % by weight.

4.) Preparation of the Phenolate Solutions

The appropriate amount of demineralized water was charged into a vessel, and the calculated amount of alkali was dissolved therein. The amount of alkali was calculated in a manner that a neutralization of the phenol to 105 mol % with potassium hydroxide was achieved, except in prior art Examples 2 and 3 where 135 mol % of potassium hydroxide were used.

Subsequently, the phenol or its derivatives was added in an amount corresponding to the required actives content of the solution in (% by wt.) and dissolved under agitation and heating to 50° C.

In the Examples according to the present invention, 1–10% by wt. of crystallization inhibitor was added depending on the experimental series.

No crystallization inhibitor was added in the Examples according to the prior art.

Afterwards, the solutions were stored in a freezer for at least 24 h and visually inspected for crystallization, 50–100 mg of the appropriate dry phenolate or phenol derivative were added as seed crystals, and the solutions were again inspected for crystallization at −20° C.

PRIOR ART EXAMPLES

Example 1

Prior Art

Test solution 30% by wt. OPP corresponding to 39% by wt. OPPK:
300.0 g o-phenylphenol
103.5 g KOH
596.5 g water Test solution 50% by wt. OPP corresponding to 66.5% by wt. OPPK:
500.0 g o-phenylphenol
173.0 g KOH
327.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C.

Results:

| Test solution | crystallization at −20° C. |
|---|---|
| 30% by wt. o-phenylphenol (OPP) (105 mol % K neutr.) | yes |
| 50% by wt. o-phenylphenol (OPP) (105 mol % K neutr.) | yes |

A solution of 30% by wt. and 50% by wt., respectively, of o-phenylphenol corresponding to 39% by wt. and 66.5% by wt. respectively, of potassium o-phenylphenolate neutralized with 1.05 mols KOH per mol o-phenylphenol in distilled water partly crystallizes spontaneously and partly after a storage for 3 days at −20° C.

Upon addition of 50 mg o-phenylphenol (OPP crystals) as seed crystals the solution spontaneously crystallizes at −20° C. forming a solid mass.

In this form, the solution is unsuitable for use. Crystallization of the solution at −20° C. can only be prevented by adding a high excess of KOH.

Example 2

Prior Art

Test solution 20% by wt. OPP corresponding to 25% by wt. OPPNa:
200.0 g o-phenylphenol
49.4 g NaOH
750.6 g water The water was charged into a vessel, NaOH was added and dissolved under agitation on a magnetic stirrer within 5 min. Afterwards, the o-phenylphenol was added and dissolved in the NaOH solution under agitation on a magnetic stirrer at 50° C.

Results:

| Test solution | crystallization at −20° C. |
|---|---|
| 20% by wt. o-phenylphenol (105 mol % Na neutr.) corresponding to 24.7% by wt. OPPNa | yes, spontaneously the freezing point is −7° C. |

A solution of 20% by wt. of o-phenylphenol corresponding to 24.7% by wt. sodium o-phenylphenolate neutralized with 1.05 mols NaOH per mol o-phenylphenol in distilled water show a spontaneous crystallization; the freezing point is only minus 7° C.

In this form, the solution is unsuitable for use.

Example 3

Prior Art

Test solution 30% by wt. OPP corresponding to 39% by wt. OPPK:
300.0 g o-phenylphenol
133.4 g KOH corresponding to 1.35 mols KOH/mol OPP
566.6 g water The water was charged into a vessel, the KOH was added and dissolved under agitation on a magnetic stirrer within 5 min. Afterwards, the o-phenylphenol was added and dissolved in the KOH solution under agitation on a magnetic stirrer at 50° C.

Result:

| Test solution | crystallization at −20° C. |
|---|---|
| Commercial 30% by wt. solution of o-phenylphenol corresponding to a 39% by wt. solution of potassium o-phenylphenolate (1.35 mol KOH/mol OPP) | no crystallization observed |

An aqueous slurry of kaolin from Georgia, USA, having a solids content of 72.8% by wt. and such a grain size distribution that 94% by wt. of the particles had a diameter of below 2 µm (as measured by Sedigraph 5100, Micromeritics, USA) dispersed with 0.35% by wt. of sodium polyacrylate and having a pH of 7.4 was added with 300 g/t of slurry, based on 100% OPP of the above commercial 39% by wt. solution or 66.5% by wt. potassium o-phenylphenolate solution, respectively, (corresponding to 300 ppm 100% OPP). A blank of the kaolin sample was prepared in the same manner but did not contain the preservative.

Results:

| | pH | Brookfield viscosity spindle 3, 100 rpm after preparation | Brookfield viscosity spindle 3, 100 rpm after 1 week |
|---|---|---|---|
| Blank without potassium o-phenylphenolate | 7.4 | 240 mPas | 330 mPas |
| Sample with 300 g of active OPP, 39% by wt. potassium o-phenylphenolate/t of slurry | 8.1 | 310 mPas | 960 mPas |

In the blank without the commercial potassium o-phenylphenolate a germ count of $10^5$/g was measured after 48 hrs.

In the sample containing 300 ppm, based on 100% OPP, of commercial the potassium o-phenylphenolate a germ count <100/g was measured after 48 hrs.

Upon addition of 300 ppm, based on 100% OPP, of the 39% by wt. commercial potassium o-phenylphenolate solution, the viscosity of the kaolin slurry having a high solids content dispersed with sodium polyacrylate increased immediately as well as during a storage period of 1 week.

In this case, there is a risk that it may be impossible to unload the slurry after shipment for several weeks in large quantities by ship, rail or truck. However, to keep the slurry sterile, it is required to use 300 ppm, based on 100% OPP, added in the form of potassium o-phenylphenolate. It is impossible to preserve the slurry without adversely affecting the other properties of the slurry.

Example 4

Prior Art

An aqueous slurry of calcium carbonate from natural marble obtained from Norway having a solids content of 77.8% by wt. and such a grain size distribution that 90% by wt. of the particles had a diameter of below 2 µm (as measured by Sedigraph 5100, Micromeritics, USA) was preserved by 250 g/t of slurry, based on 100% OPP in the form of a commercial 39% by wt. solution of potassium o-phenylphenolate as in Example 2 added dropwise under stirring within 1 min. A blank of the calcium carbonate slurry was prepared in the same manner but without preservative.

Results:

| | pH | Brookfield viscosity spindle 3, 100 rpm after preparation | Brookfield viscosity spindle 3, 100 rpm after 1 week |
|---|---|---|---|
| Blank without potassium o-phenylphenolate | 9.6 | 340 mPas | 350 mPas |
| Sample with 250 g potassium o-phenylphenolate/t | 10.4 | 320 mPas | 460 mPas |

The oversize products of the blank without commercial potassium o-phenylphenolate were 25 ppm using a screen with a mesh size of 45 µm.

The oversize products of the sample with 250 ppm, based on 100% OPP, added as the commercial potassium o-phenylphenolate were 160 ppm on a screen having a mesh size of 45 µm.

In the blank without commercial potassium o-phenylphenolate a germ count of $10^5$/g was measured after 48 hrs.

In the sample with 250 ppm/t, based on 100% OPP, added as the commercial potassium o-phenylphenolate, a germ count <100/g was measured after 48 hrs.

The viscosity of the calcium carbonate slurry having a high solids content which had been dispersed with sodium polyacrylate was not very much increased during a storage period of 1 week. However, it was clearly visible that the oversize products of the 45 μm screen were unacceptably increased. The high concentration of salt resulted in agglomerate formation in the highly concentrated slurry. The pH of the slurry was adversely altered into the more alkaline range. A pH of more than 10 in the coating used in paper industry leads to rheology problems. Furthermore, the increase in oversize products of this product inevitably leads to scratches in the paper coat as well as to dust formation during printing.

To protect the slurry from spoilage by microorganisms, it is required to add 250 ppm, based on 100% OPP, in the form of the commercial potassium o-phenylphenolate of Example 2.

It is impossible to preserve the slurry without adversely affecting the other properties of the slurry.

Example 5

Prior Art

Test solution 30% by wt. +3% monopropylene glycol:
300.0 g o-phenylphenol
103.5 g KOH
30.0 g monopropylene glycol
596.5 g water
Test solution 30% by wt. +5% monopropylene glycol:
300.0 g o-phenylphenol
103.5 g KOH
50.0 g monopropylene glycol
546.5 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol was added.

Results:

| Test solution | crystallization at −20° C. upon seeding with 100 mg OPP as seed crystals |
| --- | --- |
| 30% by wt. o-phenylphenol (OPP) (105 mol % K neutr.) | |
| with 3% monopropylene glycol | spontaneous crystallization |
| with 5% monopropylene glycol | spontaneous crystallization |

A solution of 30% by wt. of o-phenylphenol neutralized with 1.05 mols KOH per mol o-phenylphenol corresponding to 39% by wt. potassium o-phenylphenolate in distilled water shows spontaneous crystallization at −20° C. if OPP is added as seed crystals despite of the addition of 3–5% monopropylene glycol.

EXAMPLES ACCORDING TO THE PRESENT INVENTION

Example 6

Test solution 50% by wt. +1% monopropylene glycol:
500.0 g o-phenylphenol
173.0 g KOH
10.0 g monopropylene glycol
317.0 g water
Test solution 50% by wt. +3% monopropylene glycol:
500.0 g o-phenylphenol
173.0 g KOH
30.0 g monopropylene glycol
297.0 g water
Test solution 50% by wt. +5% monopropylene glycol:
500.0 g o-phenylphenol
173.0 g KOH
50.0 g monopropylene glycol
277.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol was added.

Results:

| Test solution | crystallization at −20° C. upon seeding with 100 mg OPP as seed crystals |
| --- | --- |
| 50% by wt. o-phenylphenol (OPP) (105 mol % K neutr.) | |
| with 1% monopropylene glycol | no crystallization |
| with 3% monopropylene glycol | no crystallization |
| with 5% monopropylene glycol | no crystallization |

A solution of 50% by wt. of o-phenylphenol neutralized with 1.05 mols KOH per mol o-phenylphenol corresponding to 66.5% by wt. potassium o-phenylphenolate in distilled water shows no crystallization at −20° C. even upon addition of OPP added as seed crystals if the crystallization inhibitor according to the present invention is added in the form of monopropylene glycol.

Example 7

Test solution 50% by wt. +1% 1-butanol:
500.0 g o-phenylphenol
173.0 g KOH
10.0 g 1-butanol
317.0 g water
Test solution 50% by wt. +3% 1-butanol:
500.0 g o-phenylphenol
173.0 g KOH
30.0 g 1-butanol
297.0 g water
Test solution 50% by wt. +5% 1-butanol:
500.0 g o-phenylphenol
173.0 g KOH
50.0 g 1-butanol
277.0 g water
Test solution 50% by wt. +10% 1-butanol:
500.0 g o-phenylphenol
173.0 g KOH
100.0 g 1-butanol
227.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the 1-butanol was added.

Results:

| Test solution | crystallization at −20° C. upon seeding with 100 mg OPP as seed crystals |
|---|---|
| 50% by wt. o-phenylphenol (OPP) (105 mol % K neutr.) | |
| with 1% 1-butanol | no crystallization |
| with 3% 1-butanol | no crystallization |
| with 5% 1-butanol | no crystallization |
| with 10% 1-butanol | no crystallization |

A solution of 50% by wt. of o-phenylphenol neutralized with 1.05 mols KOH per mol o-phenylphenol corresponding to 66.5% by wt. potassium o-phenylphenolate in distilled water shows no crystallization at −20° C. even upon addition of OPP added as seed crystals if the crystallization inhibitor according to the present invention is added in the form of 1-butanol.

Example 8

Test solution 50% by wt. +1% benzyl alcohol:
500.0 g o-phenylphenol
173.0 g KOH
10.0 g benzyl alcohol
317.0 g water Test solution 50% by wt. +3% benzyl alcohol:
500.0 g o-phenylphenol
173.0 g KOH
30.0 g benzyl alcohol
297.0 g water Test solution 50% by wt. +5% benzyl alcohol:
500.0 g o-phenylphenol
173.0 g KOH
50.0 g benzyl alcohol
277.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the benzyl alcohol was added.

Results:

| Test solution | crystallization at −20° C. upon seeding with 100 mg OPP as seed crystals |
|---|---|
| 50% by wt. o-phenylphenol (OPP) (105 mol % K neutr.) | |
| with 1% benzyl alcohol | no crystallization |
| with 3% benzyl alcohol | no crystallization |
| with 5% benzyl alcohol | no crystallization |

A solution of 50% by wt. of o-phenylphenol neutralized with 1.05 mols KOH per mol o-phenylphenol corresponding to 66.5% by wt. potassium o-phenylphenolate in distilled water shows no crystallization at −20° C. even upon addition of OPP added as seed crystals if the crystallization inhibitor according to the present invention is added in the form of benzyl alcohol.

Example 9

Test solution 50% by wt. +1% 1-butanol:
500.0 g o-phenylphenol
173.0 g KOH
10.0 g 1-butanol
317.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the 1-butanol was added.

An aqueous slurry of kaolin from Georgia, USA, having a solids content of 72.8% by wt. and such a grain size distribution that 94% by wt. of the particles had a diameter of below 2 $\mu$m (as measured by Sedigraph 5100, Micromeritics, USA) dispersed with 0.35% by wt. of sodium polyacrylate and having a pH of 7.4 was added with 300 g/t of slurry, based on 100% OPP, added in the form of the above 66.5% by wt. potassium o-phenylphenolate solution. A blank of the kaolin sample was prepared in the same manner but did not contain the preservative.

Results:

| | pH | Brookfield viscosity spindle 3, 100 rpm after preparation | Brookfield viscosity spindle 3, 100 rpm after 1 week |
|---|---|---|---|
| Blank without potassium o-phenylphenolate | 7.4 | 240 mPas | 330 mPas |
| Sample with 300 g actives of the 66.5% by wt. potassium o-phenylphenolate/t of slurry | 7.6 | 265 mPas | 360 mPas |

In the blank without potassium o-phenylphenolate a germ count of $10^5$/g was measured after 48 hrs.

In the sample with 300 ppm/t slurry, based on 100% OPP, added as potassium o-phenylphenolate a germ count <100/g was measured after 48 hrs.

Upon addition of 300 ppm each, based on 100% OPP, of the potassium o-phenylphenolate solution according to the present invention, the viscosity of the kaolin slurry having a high solids content dispersed with sodium polyacrylate increased only slightly. In this case, there is no risk that it may be impossible to unload the slurry after shipment in large quantities for several weeks by ship, rail or truck.

300 ppm, based on 100% OPP, of the potassium o-phenylphenolate according to the present invention are sufficient to keep the slurry sterile. It is possible to preserve the slurry without adversely affecting the other properties of the slurry.

Example 10

Test solution 50% by wt. +1% 1-butanol:
500.0 g o-phenylphenol
173.0 g KOH
10.0 g 1-butanol
317.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the 1-butanol was added.

An aqueous slurry of calcium carbonate from natural marble obtained from Norway having a solids content of 77.8% by wt. and such a grain size distribution that 90% by wt. of the particles had a diameter of below 2 μm (as measured by Sedigraph 5100, Micromeritics, USA) was preserved by 250 g/t of slurry, based on 100% OPP, of the 66.5% by wt. potassium o-phenylphenolate according to the present invention added dropwise under stirring within 1 min. A blank of the calcium carbonate slurry was prepared in the same manner but without preservative.

Results:

|  | pH | Brookfield viscosity spindle 3, 100 rpm after preparation | Brookfield viscosity spindle 3, 100 rpm after 1 week |
|---|---|---|---|
| Blank without potassium o-phenylphenolate | 9.6 | 340 mPas | 350 mPas |
| Sample with 250 g actives of 66.5% by wt. potassium o-phenylphenolate/t slurry | 9.8 | 290 mPas | 360 mPas |

The oversize products of the blank without potassium o-phenylphenolate were 28 ppm using a screen with a mesh size of 45 μm.

The oversize products of the sample with 250 ppm, based on 100% OPP, added as the 66.5% by wt. potassium o-phenylphenolate solution according to the present invention were 38 ppm on a screen having a mesh size of 45 μm.

In the blank without potassium o-phenylphenolate a germ count of $10^5$/g was measured after 48 hrs.

In the sample with 250 ppm/t of slurry, based on 100% OPP, added as potassium o-phenylphenolate according to the present invention, a germ count <100/g was measured after 48 hrs.

The viscosity of the calcium carbonate slurry having a high solids content which had been dispersed with sodium polyacrylate was not very much increased during a storage period of 1 week. The value was within the variation of the method. The oversize products of the 45 μm screen only showed a very small increase which is also within the variation of the method. The lower concentration of salt in the solution according to the present invention did not result in a considerable agglomerate formation in the highly concentrated slurry. The pH of the slurry was not substantially altered into the alkaline range. The slurry preserved with the formulations according to the present invention is suitable for the papermaking industry.

To protect the slurry from spoilage by microorganisms it is necessary to add 250 ppm, based on 100% OPP, added in the form of potassium o-phenylphenolate. By using the formulation according to the present invention, it is possible to preserve the slurry without negatively affecting other properties of the slurry.

Example 11

Test solution 50% by wt., calculated as o-phenylphenol, +3% monopropylene glycol:
500.0 g o-phenylphenol
86.5 g KOH
60.3 g NaOH
30.0 g monopropylene glycol
323.2 g water In each case, the water was charged into a vessel, KOH and NaOH were added and dissolved under agitation on a magnetic stirrer within 5 min. Afterwards, the o-phenylphenol was added and dissolved in the KOH/NaOH solution under agitation on a magnetic stirrer at 50° C. Finally, the monopropylene glycol was added.

Results:

| Test solution | crystallization at −20° C. upon seeding with 100 mg OPP as seed crystals |
|---|---|
| 50% by wt. o-phenylphenol (OPP) (52.5 mol % K neutr. and 52.5 mol % Na neutr.) with 3% monopropylene glycol | no crystallization |

A solution of 50% by wt. o-phenylphenol neutralized with 0.525 mols of KOH and 0.525 mols of NaOH per mol o-phenylphenol corresponding to about 64% by wt. potassium/sodium o-phenylphenolate in distilled water shows no crystallization at −20° C. even upon addition of OPP added as seed crystals if the crystallization inhibitor according to the present invention is added in the form of monopropylene glycol.

Example 12

Test solution 50% by wt., calculated as p-phenylphenol, +3% 1-butanol:
500.0 g o-phenylphenol
173.0 g KOH
30.0 g 1-butanol
297.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the 1-butanol was added.

Results:

| Type of seed crystals | Crystallization at −15° C. upon seeding with 100 mg of different phenols/phenolates, cresols, resorcinols, or other substances as seed crystals |
|---|---|
| with phenol in form of scales | no crystallization |
| with o-phenylphenol in form of scales | no crystallization |
| with sodium o-phenylphenolate in form of scales | no crystallization |
| with potassium o-phenylphenolate as a powder | no crystallization |
| with 4-isopropyl-m-cresol as a powder | no crystallization |
| with 4-n-hexylresorcinol as a powder | no crystallization |
| with silica sand in powder form (50% by wt. <2 μm) | no crystallization |
| with o-phenylphenol and silica sand in powder form (50% by wt. <2 μm) | no crystallization |

A solution of 50% by wt. of o-phenylphenol neutralized with 1.05 mols of KOH per mol o-phenylphenol corresponding to 66.5% by wt. potassium o-phenylphenolate in distilled water shows no crystallization at minus 15° C. even upon addition of different types of seed crystals if the crystallization inhibitor according to the present invention is added in the form of 3% by wt. 1-butanol.

Example 13

Test solution 40% by wt. +10% each of different crystallization inhibitors:
400.0 g o-phenylphenol
138.4 g KOH
100.0 g monopropylene glycol or 1-butanol or benzyl alcohol, respectively
361.6 g water In each case, the water was charged into a vessel, KOH were added and dissolved under agitation on a magnetic stirrer within 5 min. Afterwards, the o-phenylphenol was added and dissolved in the KOH solution under agitation on a magnetic stirrer at 50° C. Finally, the crystallization inhibitor was added.

Results:

| Test solution | crystallization at −10° C. upon seeding with 100 mg OPP as seed crystals |
|---|---|
| 40% by wt. o-phenylphenol (OPP) (105 mol % K neutr.) | |
| with 10% monopropylene glycol | no crystallization |
| with 10% 1-butanol | no crystallization |
| with 10% benzyl alcohol | no crystallization |

A solution of 40% by wt. of o-phenylphenol neutralized with 1.05 mols of KOH per mol o-phenylphenol corresponding to 53% by wt. potassium o-phenylphenolate in distilled water shows no crystallization at −10° C. even upon addition of OPP added as seed crystals if the crystallization inhibitor according to the present invention is added in the form of monopropylene glycol or 1-butanol or benzyl alcohol, respectively.

Example 14

Test solution 50% by wt. +5% monopropylene glycol:
500.0 g phenol
312.8 g KOH
50.0 g monopropylene glycol
137.2 g water In each case, the water was charged into a vessel, KOH was added and dissolved under agitation on a magnetic stirrer within 5 min. Afterwards, the phenol was added and dissolved in the KOH solution under agitation on a magnetic stirrer at 50° C. Finally, the monopropylene glycol was added.

Results:

| Test solution | crystallization at −20° C. upon seeding with 100 mg OPP as seed crystals |
|---|---|
| 50% by wt. phenol (105 mol % K neutr.) with 5% monopropylene glycol | no crystallization |

Example 15

Test solution 50% by wt. +5% monopropylene glycol:
500.0 g o-cresol
272.2 g KOH
50.0 g monopropylene glycol
177.8 g water In each case, the water was charged into a vessel, KOH was added and dissolved under agitation on a magnetic stirrer within 5 min. Afterwards, the o-cresol was added and dissolved in the KOH solution under agitation on a magnetic stirrer at 50° C. Finally, the monopropylene glycol was added.

Results:

| Test solution | crystallization at −20° C. upon seeding with 100 mg OPP as seed crystals |
|---|---|
| 50% by wt. o-cresol (105 mol % K neutr.) with 5% monopropylene glycol | no crystallization |

Example 16

Test solution 50% by wt. +5% monopropylene glycol +0.2% oxidation inhibitor:
500.0 g o-phenylphenol
173.0 g KOH
50.0 g monopropylene glycol
2.0 g 2-phosphono-1,2,4-butanetricarboxylic acid 275.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol and the oxidation stabilizer were added.

Results:

| Test solution | crystallization at −20° C. upon seeding with 100 mg OPP as seed crystals |
|---|---|
| 50% by wt. o-phenylphenol (OPP) (105 mol % K neutr.) with 5% monopropylene glycol | no crystallization |

A solution of 50% by wt. of o-phenylphenol neutralized with 1.05 mols of KOH per mol o-phenylphenol corresponding to 66.5% by wt. potassium o-phenylphenolate in distilled water shows no crystallization at −20° C. even upon addition of OPP added as seed crystals if the crystallization inhibitor according to the present invention is added in the form of monopropylene glycol. The properties of the formulation are not adversely affected by the oxidation stabilizer.

Example 17

Test solution 50% by wt. +5% monopropylene glycol +0.05% chelating agent:
500.0 g o-phenylphenol
173.0 g KOH
50.0 g monopropylene glycol 0.5 g ethylenediaminetetraacetic acid—disodium salt (EDTA)

276.0 g water

In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol and the chelating agent were added.

Results:

| Test solution | crystallization at −20° C. upon seeding with 100 mg OPP as seed crystals |
| --- | --- |
| 50% by wt. o-phenylphenol (OPP) (105 mol % K neutr.) with 5% monopropylene glycol | no crystallization |

A solution of 50% by wt. of o-phenylphenol neutralized with 1.05 mols of KOH per mol o-phenylphenol corresponding to 66.5% by wt. potassium o-phenylphenolate in distilled water shows no crystallization at −20° C. even upon addition of OPP added as seed crystals if the crystallization inhibitor according to the present invention is added in the form of monopropylene glycol. The properties of the formulation are not adversely affected by the chelating agent.

Example 18

Test solution 50% by wt. +5% monopropylene glycol +1% of a substance promoting the biocidal effect:

500.0 g o-phenylphenol
173.0 g KOH
50.0 g monopropylene glycol
10.0 g peptone
267.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol and the substance promoting the biocidal effect were added.

Results:

| Test solution | crystallization at −15° C. upon seeding with 100 mg OPP as seed crystals |
| --- | --- |
| 50% by wt. o-phenylphenol (OPP) (105 mol % K neutr.) with 5% monopropylene glycol and 1% of substance promoting the biocidal effect | no crystallization |

A solution of 50% by wt. of o-phenylphenol neutralized with 1.05 mols of KOH per mol o-phenylphenol corresponding to 66.5% by wt. potassium o-phenylphenolate in distilled water shows no crystallization at −15° C. even upon addition of OPP added as seed crystals if the crystallization inhibitor according to the present invention is added in the form of monopropylene glycol. The properties of the formulation are not adversely affected by the peptone.

Example 19

Test solution 50% by wt. +7% monopropylene glycol +3% additional substance having a biocidal effect:

500.0 g o-phenylphenol
173.0 g KOH
70.0 g monopropylene glycol
50.0 g N-tallow-1,3-diaminopropane
207.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol and the additional substance having a biocidal effect were added.

Results:

| Test solution | crystallization at −15° C. upon seeding with 100 mg OPP as seed crystals |
| --- | --- |
| 50% by wt. o-phenylphenol (OPP) (105 mol % K neutr.) with 7% monopropylene glycol and 5% of the additional substance having a biocidal effect | no crystallization |

A solution of 50% by wt. of o-phenylphenol neutralized with 1.05 mols of KOH per mol o-phenylphenol corresponding to 66.5% by wt. potassium o-phenylphenolate in distilled water shows no crystallization at −15° C. even upon addition of OPP added as seed crystals if the crystallization inhibitor according to the present invention is added in the form of monopropylene glycol. The properties of the formulation are not adversely affected by the additional biocide.

Example 20

Test solution 50% by wt. +3% monopropylene glycol+500.0 g trichlorophenol 150.0 g KOH
30.0 g monopropylene glycol
320.0 g water In each case, the water was charged into a vessel, KOH was added and dissolved under agitation on a magnetic stirrer within 5 min. Afterwards, the trichlorophenol was added and dissolved in the KOH solution under agitation on a magnetic stirrer at 50° C. Finally, the monopropylene glycol was added.

Results:

| Test solution | crystallization at −15° C. upon seeding with 100 mg OPP as seed crystals |
| --- | --- |
| 50% by wt. trichlorophenol (105 mol % K neutr.) with 3% monopropylene glycol | no crystallization |

A solution of 50% by wt. of trichlorophenol neutralized with 1.05 mols of KOH per mol trichlorophenol corresponding to 60% by wt. potassium trichlorophenolate in distilled water shows no crystallization at −15° C. even upon addition of OPP added as seed crystals if the crystallization inhibitor according to the present invention is added in the form of monopropylene glycol.

Example 21

Test solution 50% by wt. +5% monopropylene glycol +5% of an additional substance having a biocidal effect:
500.0 g o-phenylphenol
173.0 g KOH
50.0 g monopropylene glycol
50.0 g sodium salicylate
227.0 g water In each case, the water was charged into a vessel, KOH was added and dissolved under agitation on a magnetic stirrer within 5 min. Afterwards, the o-phenylphenol was added and dissolved in the KOH solution under agitation on a magnetic stirrer at 50° C. Finally, the monopropylene glycol was added.

Results:

| Test solution | crystallization at −15° C. upon seeding with 100 mg OPP as seed crystals |
|---|---|
| 50% by wt. o-phenylphenol (OPP) (105 mol % K neutr.) with 5% monopropylene glycol and 5% of the additional substance having a biocidal effect | no crystallization |

A solution of 50% by wt. of o-phenylphenol neutralized with 1.05 mols of KOH per mol o-phenylphenol corresponding to 66.5% by wt. potassium o-phenylphenolate in distilled water shows no crystallization at −15° C. even upon addition of OPP added as seed crystals if the crystallization inhibitor according to the present invention is added in the form of monopropylene glycol. The properties of the formulation are not adversely affected by the additional biocide.

Example 22

Test solution 50% by wt. +5% monopropylene glycol:
500.0 g o-cresol
174.9 g KOH
50.0 g monopropylene glycol
275.1 g water In each case, the water was charged into a vessel, KOH was added and dissolved under agitation on a magnetic stirrer within 5 min. Afterwards, the o-cresol was added and dissolved in the KOH solution under agitation on a magnetic stirrer at 50° C. Finally, the monopropylene glycol was added.

Results:

| Test solution | crystallization at −15° C. upon seeding with 100 mg o-cresol as seed crystals |
|---|---|
| 50% by wt. o-cresol (105 mol % K neutr.) with 5% monopropylene glycol | no crystallization |

A solution of 50% by wt. of o-cresol neutralized with 1.05 mols of KOH per mol o-phenylphenol corresponding to 61.6% by wt. o-cresol potassium salt in distilled water shows no crystallization at −15° C. even upon addition of o-cresol added as seed crystals if the crystallization inhibitor according to the present invention is added in the form of monopropylene glycol.

What is claimed is:

1. An aqueous, phenolate-containing liquid formulation, comprising:
    a) 50–80% by wt. of one or more phenolates;
    b) 0.1–10% by wt. of at least one crystallization inhibitor;
    c) water; and
    d) optionally a balance of at least one other component having a biocidal effect and/or promoting a biocidal effect of said one or more phenolates;
    wherein said aqueous, phenolate-containing liquid formulation has a solidification point of less than or equal to −10° C.;
    wherein said one or more phenolates are present in a form selected from the group consisting of a potassium salt, a mixture of a potassium salt and a sodium salt, a mixture of a potassium salt and a lithium salt and mixtures thereof.

2. The aqueous, phenolate-containing liquid formulation according to claim 1, which comprises as said one or more phenolates a member selected from the group consisting of salts of phenol, phenolates having one or more aliphatic substituents, phenolates having one or more aromatic substituents mixtures of salts of phenol and phenolates having one or more aliphatic substituents, mixtures of salts of phenol and phenolates having one or more aromatic substituents, and mixtures thereof.

3. The aqueous, phenolate-containing liquid formulation according to claim 1, which comprises as said one or more phenolates a member selected from the group consisting of o-phenylphenolates, halogenated phenolates, cresol salts, salts of halogenated cresols, resorcinol salts and mixtures thereof.

4. The aqueous, phenolate-containing liquid formulation according to claim 3, which comprises as the cresol salts a member selected from the group consisting of salts of o-cresol, salts of m-cresol, salts of p-cresol, salts of isopropyl o-cresol, salts of 4-isopropyl m-cresol, halogenated cresols, and
    as the resorcinol salts a member selected from the group consisting of salts of 4-n-hexyl resorcinol.

5. The aqueous, phenolate-containing liquid formulation according to claim 1, which comprises one or more phenolates in an amount of 50–75% by wt.

6. The aqueous, phenolate-containing liquid formulation according to claim 1, which comprises said at least one crystallization inhibitor in an amount of 0.5–5% by wt.

7. The aqueous, phenolate-containing liquid formulation according to claim 1, said formulation containing as the crystallization inhibitor a member selected from the group consisting of one or more aliphatic glycol compound(s), one or more aliphatic alcohol(s), one or more aromatic alcohol(s), and mixtures thereof.

8. The aqueous, phenolate-containing liquid formulation according to claim 1, which comprises a member selected from the group consisting of organometal compounds, quaternary ammonium compounds and mixtures thereof, and/or a member selected from the group consisting of chelating agents, antioxidants and mixtures thereof.

9. The aqueous, phenolate-containing liquid formulation according to claim 1, which comprises a member selected from the group consisting of dicocomethylbenzylammonium chloride, tributyl tin benzoate, N-tallow-1,3-diaminopropane and mixtures thereof.

10. The aqueous, phenolate-containing liquid formulation according to claim 1, which comprises 0.05–1% by wt. based on the formulation of a member selected from the group consisting of NTA, EDTA, DTPA, 2-phosphono-1,2,4-butanetricarboxylic acid and mixtures thereof.

11. The aqueous, phenolate-containing liquid formulation according to claim 1, which comprises
   a) 50–80% by wt. of at least one phenolate; and
   b) 20–50% by wt. of a solvent system comprising 90–99% by wt. water and 0.1–10.0% by wt. of at least one crystallization inhibitor;
   wherein a proportion of 1.0–4.9% by wt. of said formulation may be replaced by additional microbicidal agents and/or at least one component promoting a microbicidal effect of said phenolate or a microbicidal effect of said additional microbicidal agent.

12. The aqueous, phenolate-containing liquid formulation according to claim 1, wherein said one or more phenolates are dissolved in a solvent system and are neutralized with an excess of 0.03–0.15 mols of at least one alkali hydroxide, based on the amount of phenolates.

13. The aqueous, phenolate-containing liquid formulation according to claim 12, wherein 1.03–1.15 of alkali hydroxide per mol of phenolate are used for neutralization.

14. The aqueous, phenolate-containing liquid formulation according to claim 1, wherein the crystallization inhibitors are present in an amount of 1–3% by wt. in a formulation containing 60–70% by wt. of one or more phenolates.

15. The aqueous, phenolate-containing liquid formulation according to claim 1, comprising:
   50–80% by wt. of said one or more phenolates;
   0.1–10% by wt. of a crystallization inhibitor selected from the group consisting of one or more aliphatic glycol compound(s), glycerol, one or more aliphatic alcohol(s), one or more aromatic alcohol(s) and mixtures thereof; and
   a balance with respect to 100% by wt. comprising alkali in an excess of 0.03–0.15 mol/mol and water.

16. The aqueous, phenolate-containing liquid formulation according to claim 4, wherein said halogenated cresol is chlorinated cresols.

17. The aqueous, phenolate-containing liquid formation according to claim 1, which comprises one or more phenolates in an amount of 55–70% by wt.

18. The aqueous, phenolate-containing liquid formulation according to claim 1, which comprises one or more phenolates in an amount of 60–70% by wt.

19. The aqueous, phenolate-containing liquid formulation according to claim 1, which comprises one or more phenolates in an amount of 62–67% by wt.

20. The aqueous, phenolate-containing liquid formulation according to claim 1, which comprises the crystallization inhibitors in an amount of 1–3% by wt.

21. The aqueous, phenolate-containing liquid formulation according to claim 7, wherein said one or more aliphatic glycol compound(s) are a member selected from the group consisting of ethylene glycol, monopropylene glycol, diethylene glycol and mixtures thereof.

22. A method for the preparation of an aqueous, phenolate-containing liquid formulation, according to claim 1 comprising:
   placing water and a neutralizing agent in a vessel;
   dissolving a phenol compound; and
   adding a crystallization inhibitor.

23. The aqueous, phenolate-containing liquid formulation according to claim 7, wherein said one or more aromatic alcohol(s) are a member selected from the group consisting of benzyl alcohol, 2-phenylethane-1-ol, 3-phenylpropane-1-ol, 1-phenylpropane-2-ol and mixtures thereof.

24. An aqueous suspension or dispersion, comprising: a member selected from the group consisting of minerals, fillers, pigments, natural organic binders, synthetic organic binders, cooling lubricants and mixtures thereof, and
   the aqueous, phenolate-containing liquid formulation according to claim 1.

25. The aqueous suspension or dispersion according to claim 14, wherein said aqueous, phenolate-containing liquid formulation is present in an amount of 100 g/ton to 2500 g/ton of the suspension or dispersion.

26. A preservative and/or mordant, comprising:
   the aqueous, phenolate-containing liquid formulation according to claim 1.

27. The aqueous, phenolate-containing liquid formulation according to claim 7, wherein said one or more aliphatic alcohol(s) are a member selected from the group consisting of methanol, ethanol, n-propanol, iso-propanol, isomers of butanol, isomers of pentanol and mixtures thereof.

28. The method according to claim 27, comprising:
   placing the crystallization inhibitor together with the water and the neutralizing agent in a vessel, and afterwards dissolving the phenol compound therein.

29. The method according to claim 27, wherein a temperature during dissolving is 5–80° C.

* * * * *

UNITED STATES PATENT AND TRADEMARK OFFICE
CERTIFICATE OF CORRECTION

PATENT NO.       : 6,994,798 B2
APPLICATION NO.  : 10/275861
DATED            : February 7, 2006
INVENTOR(S)      : Matthias Buri et al.

It is certified that error appears in the above-identified patent and that said Letters Patent is hereby corrected as shown below:

Column 4, line 32, "quatemary" should read --quaternary--

Column 4, line 33, "quatemary" should read --quaternary--

Column 22, line 20, "form selected" should read --form of a salt having a cation selected--

Column 22, line 28, "of salts of phenol, phenolates" should read --of phenolates--

Column 24, line 31, "14" should read --24--

Column 24, line 43, "27" should read --22--

Column 24, line 47, "27" should read --22--

Signed and Sealed this

Seventh Day of November, 2006

JON W. DUDAS
*Director of the United States Patent and Trademark Office*